United States Patent [19]

Munro et al.

[11] Patent Number: 4,874,767
[45] Date of Patent: Oct. 17, 1989

[54] DISCORHABDIN D, COMPOSITIONS CONTAINING SAME AND METHODS OF PREPARATION AND USE THEREOF

[75] Inventors: Murray H. G. Munro; Nigel B. Perry; John W. Blunt, all of Christchurch, New Zealand

[73] Assignee: Harbor Branch Oceanographic Institution, Inc., Ft. Pierce, Fla.

[21] Appl. No.: 294,394

[22] Filed: Jan. 9, 1989

[51] Int. Cl.[4] .................. A61K 31/395; A61K 31/38; C07D 513/22; C07D 495/99
[52] U.S. Cl. ........................................ 514/278; 546/18
[58] Field of Search .......................... 546/18; 514/278

[56] References Cited

U.S. PATENT DOCUMENTS 4,731,366 3/1988 Munro et al. .................... 546/18

Primary Examiner—Robert T. Bond
Attorney, Agent, or Firm—Carroll F. Palmer

[57] ABSTRACT

A new biologically active compound discorhabdin D, pharmaceutical compositions containing same, methods of producing the compound and compositions and methods of using them are disclosed. The new compound, discorhabdin D, has the structure:

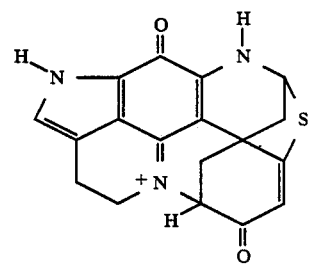

4 Claims, No Drawings

DISCORHABDIN D, COMPOSITIONS CONTAINING SAME AND METHODS OF PREPARATIO AND USE THEREOF

FIELD OF THE INVENTION

This application relates to the novel compound discorhabdin D and compositions containing such compound as an active ingredient. More particularly, the invention concerns the new biologically active compound discorhabdin D, pharmaceutical compositions containing same, methods of producing the compound and compositions and method of using them.

BACKGROUND OF THE INVENTION

Considerable research and resources have been devoted to oncology and antitumor measures including chemotherapy. While certain methods and chemical compositions have been developed which aid in inhibiting, remitting or controlling the growth of tumors, new methods and antitumor chemical compositions are needed.

It has been found that some natural products and organisms are potential sources for chemical molecules having useful biological activity of great diversity. Marine sponges have proved to be such a source and a number of publications have issued disclosing organic compounds derived from marine sponges including Scheuer, P. J. Ed., Marine Natural Products, Chemical and Biological Perspectives; Academic Press, New York, 1978, Vol. I, pp 175-240; Faulkner, D. J., Natural Products Reports 1987, 4, 539-576 and references cited therein; Uemura et al., J. Am. Chem. Soc., 1985, 107, 4796-4798; Minale, L., et al., Fortschr. Chem. org. Naturst. 1976, 33, 1-72.

Discorhabdin compounds related to those of this invention have been produced from marine sponges as disclosed in U.S. No. 4,731,366 and have been discussed in various publications including:

Perry, N. B., et al., *J. Org. Chem.* 1986, 51, 5476; Blunt, J. W., et al., *J. Nat. Prod.* 1987, 50, 290; Munro, M. H. G., et al., *Bioorganic Marine Chemistry;* Scheuer, P. J., Ed.; Verlag Chemie: Heidelberg, 1987, Vol. 1, Chapter 4; Kobayashi, J., et al., *Tetrahedron Letters* 1987, 28, 4939; Perry, N. B., et al., *Tetrahedron* 1988, 44, 1727, Perry N. B., et al., *J. Org. Chem.* 1988, 53, 4127 and Cheng et al., *J. Org. Chem.* 1988, 53, 4610.

This present invention, utilizing sponges as a source material and supplemented by specific production methods, has provided the art with a new biologically active compound and new pharmaceutical compositions useful as antitumor agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects of the invention are accomplished by the provision of a novel, biologically active compound that has a structure according to the formula:

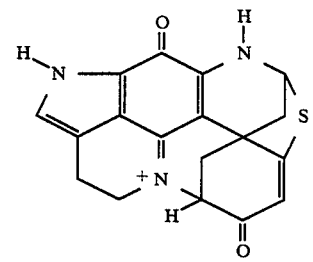

As embodied and fully described herein, the invention also comprises pharmaceutical compositions, e.g., antitumor compositions, containing as active ingredient, an effective amount, e.g., between about 0.1 to 45% by weight based on the total weight of the composition, preferably about 1 to 25% b/w, of the new compound of the invention and a non-toxic pharmaceutically acceptable carrier or diluent.

As embodied and fully described herein, the invention also comprises processes for the production of the new compound and compositions of the invention and methods of use thereof, e.g., methods of inhibiting tumors in a mammal and therapeutic methods for treating cancerous cachexia.

In accordance with the invention, methods for inhibiting tumors in a host comprise contacting tumor cells with an effective amount of the new pharmaceutical compositions of the invention.

DESCRIPTION OF THE PREFERRED EMBODIMENTS

A more complete understanding of the invention can be obtained by reference to preferred embodiments of the invention which are illustrated by the following specific examples of the new compound, compositions and methods of the invention. It will be apparent to those skilled in the art that the examples involve use of materials and reagents that are commercially available from known sources, e.g., chemical supply houses, so no details are given respecting them.

One method of preparation of the new compound of the invention involves extraction from marine sponge species of the genus Latrunculia (family Latrunculiidae, order Hadromerida).

EXAMPLE 1

This example concerns the preparation of the compound 1 of the invention, discorhabdin D, having the structure of the formula:

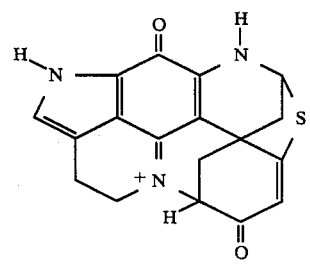

Specimens of marine sponge *L. brevis* were collected by SCUBA at depths of about 30 m from the Sugar Loaf Islands, Taranaki, New Zealand. Voucher specimens 5NP3-1 and 5NP5-7 have been deposited in the University of Canterbury Marine Collection at Christ-church, New Zealand.

The collected sponge specimens were blended and extracted with MeOH and MeOH/toluene (3:1) to give, after removal of solvents, a green gum. This was partitioned on a reverse phase (RP) column to give a combined fraction containing largely discorhabdin A 2 (see U.S. Pat. No. 4,731,366).

Preparation RPLC [Merck Lobar RP-8 column, 310×25 mm; 4 mL/min MeOH/H$_2$O (with 0.05% CF$_3$COOH) (3:7); 254 nm detectional] on a subsample gave initially 1 followed by 2. Further preparative RPLC gave pure 1.

Discorhabdin D was characterized as its hydrochloride salt, a deep green solid, mp>360° C.; $[]_D$0, $[]_{578}$ −45, $[]_{546}$ −160 (c 0.15, MeOH).

HRFABMS: MH+ found 336.08208, calcd for C$_{18}$H$_{14}$N$_3$O$_2$S 336.08069. The compound revealed the following spectral data:

UV(MeOH): 248 nm (log 4.35), 281(4.15), 320(3.93), 395(3.95), 584(2.84). UV(MeOH/KOH): 262 nm (log 4.49), 290(4.19), 368(3.98).

IR: 3700–2300, 1650, 1620, 1550, 1525, 1490, 1410, 1310 cm$^{-1}$.

$^1$H NMR (CD$_3$OD): 7.10(d, J=1.0 Hz, H14), 6.07(t, 0.8, H4), 5.60(dd, 1.4, 3.4, H8), 4.35(t, 2.8, H2), 4.0(ddd, 3.3, 7.6, 14.3, H17), 3.9(ddd, 6.8, 12.6, 14.3, H17.), 3.2(dddd, 1.1, 7.8, 12.5, 16.9, H16), 3.1(ddd, 3.2, 7.2, 16.6, H16), 2.91(dd, 2.8, 13.5, H1R), 2.80(dd, 3.6, 11.9, H7), 2.64(dd, 1.3, 12.1, H7), 2.58(dd, 3.1, 13.3, H1S).

$^1$H NMR ([CD$_3$]$_2$SO): 7.37(s, H14), 6.22(s, H4), 5.79(s, H8), 4.47(s, H2), 13.45(s, NH13), 10.8(s, NH9), 4.13(m, H17), 3.92(m, H17), 3.15(m, H16), 3.02(d, 12.8, H1R), 2.65(d, 12.8, H7), 2.55(d, 12.8, H1S).

$^{13}$C NMR ([CD$_3$]$_2$SO): 183.08(s, C3), 173.14(s, C5), 166.47(s, C11), 147.84(s, C10 or C19), 145.90(s, C19 or C10), 127.00(d, $^1J_{CH}$=190 Hz, C14), 123.69(s, C12 or C21) 121.50(s, C21 or C12), 117.71(s, C15), 112.43(d, 168, C4), 99.64(s, C20), 62.79(d, 169, C8), 62.26(d, 159, C2), 51.24(t, 145, C17), 41.19(s, C6), 38.59(t, C7), 30.27 (t, 137, C1), 19.49(t, 134, C16).

The structure as established by this spectral data and as given by the above formula, although based on the same ring system as discorhabdin C, possesses two further heterocyclic rings to give a total of seven interlocking rings (four heterocyclic and one spiro) and seven double bonds. high resolution FABMS established a composition of C$_{18}$H$_{14}$N$_3$O$_2$S for MH+ of discorhabdin D.

In-Vivo Assay For Antitumor Activity

The following procedure was used for the In-Vivo assay of discorhabdin D for P388.

P388 leukemia was maintained by serial passage in DBA/2 mice. To assay antitumor activity of Discorhabdin D, tumors were established (10$^6$ cells/0.1 ml) by injection in the i.p. cavity of BDF1 mice. Mice were randomized on day 1 into groups of six mice since bacteriological check of tumor was negative. Test materials were dissolved or suspended in sterile 0.98% NaCl solution with the aid of absolute ethanol and "Tween-80", then administered ip, qD1-9, in a volume of 0.5 ml/mouse. Mice were weighed on days 1 & 9 to provide evidence of toxicity and deaths were recorded daily. Each test included appropriate numbers of untested control mice, one-dose level of the positive reference compound 5-fluorouracil and test material (four dose levels each). Test material were prepared fresh on day 1 and administered daily for nine days. Quantity and consistency of test material precluded fresh preparation daily. Doses were derived from prior single treatment acute toxicity assays. The endpoints for therapeutic evaluation were mean and median survival time and long-term survivors on day 30. A 25% percent increase in life span (%ILS) was considered evidence of significant activity.

The following table reports the in vivo antitumor assay results for dischorhabdin D.

TABLE

| Dose mg/kg | Treatment (days) | Survival % T/C |
|---|---|---|
| 40 | 1-1 | 77 |
| 20 | 1-9 | 132 |
| 10 | 1-9 | 123 |
| 5 | 1-9 | 118 |

It is apparent from the in vivo testing and results reported in the table that the compound of the invention is effective for inhibiting or destroying tumors and therefore in controlling diseases caused by or related to such tumors, e.g., cancerous cachexia.

The embodiments of the invention in which an exclusive property or privilege is claimed are defined as follows:

1. The compound of the formula:

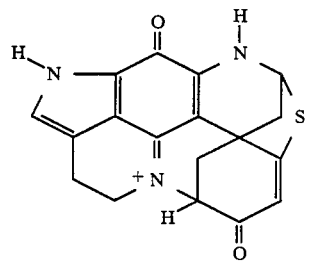

2. The compound of claim 1 which is substantially pure.

3. A pharmaceutical composition comprising a nontoxic pharmaceutically acceptable carrier or diluent and between about 0.1% to 45% by weight, based on the total weight of said composition, as an active ingredient, the compound of the formula:

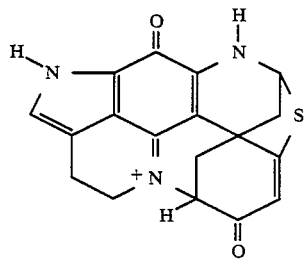

4. A pharmaceutical composition comprising a nontoxic pharmaceutically acceptable carrier or diluent and between about 1% to 25% by weight, based on the total weight of said composition, as an active ingredient, the compound of claim 1.

* * * * *

UNITED STATES PATENT AND TRADEMARK OFFICE
CERTIFICATE OF CORRECTION

PATENT NO. : 4,874,767

DATED : October 17, 1989

INVENTOR(S) : Murray H.G. Munro, Nigel B. Perry, John W. Blunt

It is certified that error appears in the above-identified patent and that said Letters Patent is hereby corrected as shown below:

Column 1: line 4: "PREPARATIO" should read --PREPARATION--.

Column 3: line 1: "Christ-church" should read --Christchurch--; line 9: "Preparation" should read --Preparative--; line 47: "high" should read --High--.

Signed and Sealed this

Second Day of July, 1991

Attest:

HARRY F. MANBECK, JR.

*Attesting Officer*       *Commissioner of Patents and Trademarks*

UNITED STATES PATENT AND TRADEMARK OFFICE
CERTIFICATE OF CORRECTION

PATENT NO. : 4,874,767

DATED : October 17, 1989

INVENTOR(S) : Murray H.G. Munro, Nigel B. Perry, John W. Blunt

It is certified that error appears in the above-identified patent and that said Letters Patent is hereby corrected as shown below:

Column 1: line 49: "4610" should read --4621--.

Column 3: line 11: "detectional" should read --detection--; line 15: "$[]_D 0, []_{578}$" should read --$[\alpha]_D 0°, [\alpha]_{578}$--; line 16: "--45, $[]_{546}$ --160" should read ---45°, $[\alpha]_{546}$ --160°--; line 20: "(log 4.35)" should read --(log $\epsilon$ 4.35)--; line 21: "(log" should read --(log $\epsilon$--; line 34: "H1R), 2.65" should read --H1R), 2.80 (d, 12.8, H7), 2.65--.

Column 4: line 11: "dischorhabdin" should read --discorhabdin--; line 14: (Table) "1-1" should read --1-9--.

Signed and Sealed this

Sixteenth Day of June, 1992

*Attest:*

DOUGLAS B. COMER

*Attesting Officer*     *Acting Commissioner of Patents and Trademarks*